United States Patent
Comello et al.

(10) Patent No.: US 6,196,075 B1
(45) Date of Patent: Mar. 6, 2001

(54) DEVICE FOR INSPECTION OF PIPES

(75) Inventors: Corry Comello, Scarborough; Poul Laursen; Jukka Maki, both of North York, all of (CA)

(73) Assignee: Pipetronix GmbH, Stutensee (DE)

( * ) Notice: Subject to any disclaimer, the term of this patent is extended or adjusted under 35 U.S.C. 154(b) by 0 days.

(21) Appl. No.: 09/173,443

(22) Filed: Oct. 16, 1998

(30) Foreign Application Priority Data

Oct. 22, 1997 (DE) ............................................. 197 46 511

(51) Int. Cl.[7] ......................................................... G01R 3/12
(52) U.S. Cl. ............................................................. 73/865.8
(58) Field of Search ............................... 73/866.5, 865.8, 73/623; 324/220

(56) References Cited

U.S. PATENT DOCUMENTS

| | | | |
|---|---|---|---|
| 3,460,028 | * 8/1969 | Beaver et al. | ......................... 324/220 |
| 3,786,684 | * 1/1974 | Wiers et al. | . |
| 4,055,990 | * 11/1977 | Topping | .................................. 73/623 |
| 4,769,598 | * 9/1988 | Krieg et al. | ............................. 73/623 |

* cited by examiner

*Primary Examiner*—Robert Raevis
(74) *Attorney, Agent, or Firm*—Paul Vincent

(57) ABSTRACT

In order to facilitate introduction of an inspection pig through an introductory conduit having a smaller diameter and into a pipeline of large diameter and transporting a fluid, in particular gas or oil, the invention proposes a device for inspection of pipes having sensors disposed about an outer periphery thereof having radially expandable inspection units (6, 7), wherein, in particular, a front and a rear inspection unit (6, 7) having sensors (15; 15') displaced with respect to each other in a peripheral sense can be moved axially towards each other.

12 Claims, 12 Drawing Sheets

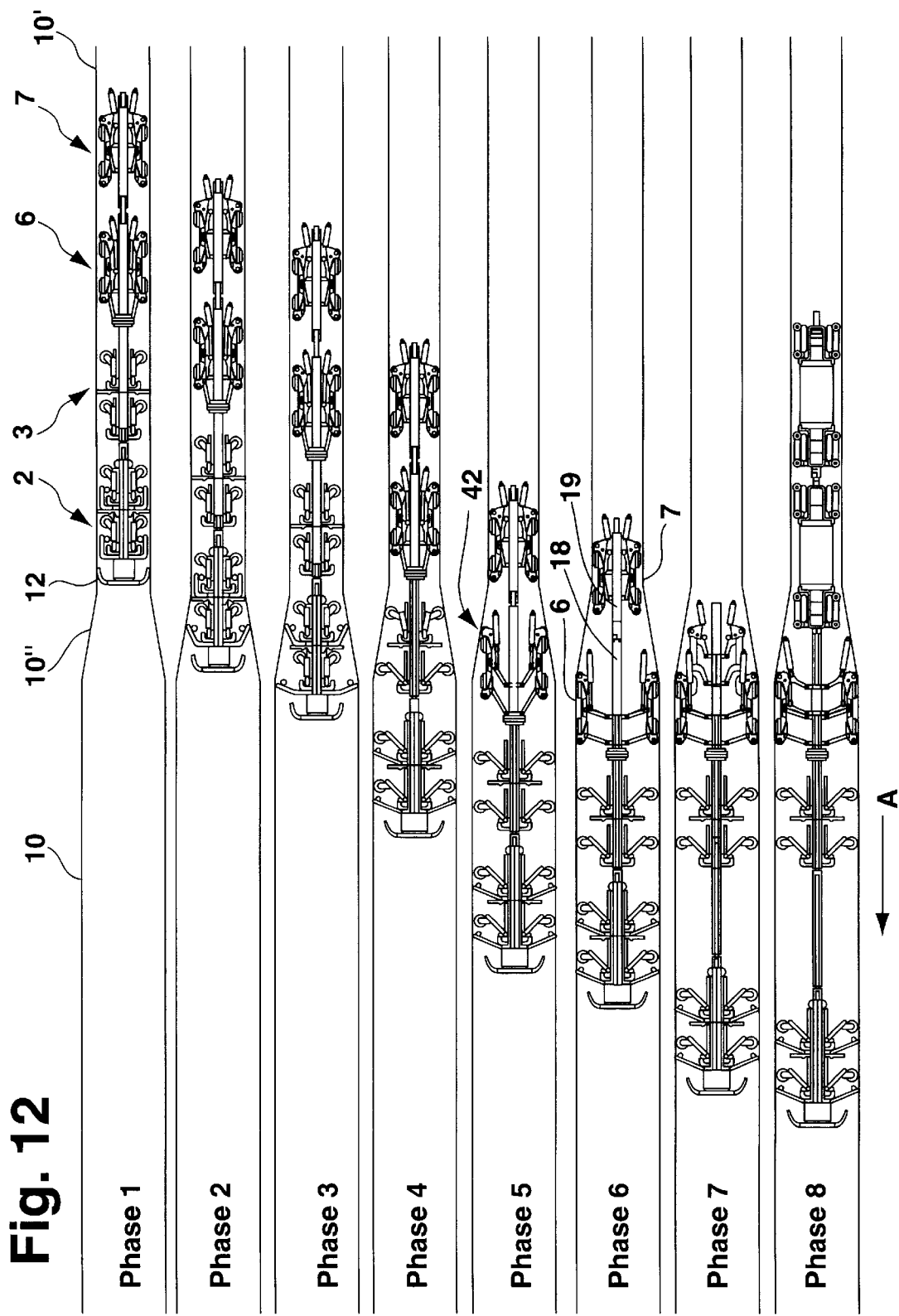

DEVICE FOR INSPECTION OF PIPES

This application claims Paris Convention Priority of German Patent application number 197 46 511.0 filed Oct. 22 1997, the complete disclosure of which is hereby incorporated by reference.

BACKGROUND OF THE INVENTION

The invention concerns a device for the inspection of pipes having sensors disposed about an outer periphery.

In order to inspect pipelines, in particular those under water or pipelines traveling below the earth, conventional so-called inspection pigs are utilized having inspection devices with inspection elements or sensors disposed about an outer girth by means of which the condition of the walls of the pipes can be inspected. The sensors can be effected in differing manners; piezoelectric sensors, Electro-acoustic sensors electromagnetic sensors such as Hall sensors, stray field sensors and eddy current sensors are all known in the art. Differing wall conditions, e.g. due to corrosion etc. provide differing signals to be further processed in an electronics unit.

Particularly for the case of conduits traveling under water, it is extremely expensive to provide an input location and extremely difficult to introduce an inspection pig into such a conduit. For example, difficult and expensive input lock mechanisms having expensive valves must be provided for. For introduction, a diver must submerge to substantial depths to introduce such a pig into a pipeline so that the pig can travel through and inspect same. On the other hand, this type of pipeline can have a relatively large diameter, on the order of the magnitude of e.g. 40 inches (corresponding to 1 m), and therefore cannot be passed from the ground to the upper surface of the water, since its weight is prohibitive.

It is the underlying purpose of the invention to create a device for the inspection of pipelines which avoids the above mentioned disadvantages and facilitates, in particular, a simple introduction into the pipeline.

SUMMARY OF THE INVENTION

This purpose is solved in accordance with the invention using a device for the inspection of pipes having sensors disposed about an outer girth thereof which is characterized by radially expandable inspection units.

The solution in accordance with the invention allows a pig to be passed through an introductory pipe having a smaller diameter, e.g. a diameter of 16 or 28 inches (corresponding to approximately 40 and 70 cm, respectively) and introduced to the main conduit having the above mentioned diameter, whereas the pig has a smaller diameter than the introductory conduit and can expand to the larger diameter of the main conduit passing the medium while nevertheless permitting a reliable inspection of the pipe conduit by means of the sensors disposed around its outer girth (in the respective expanded position).

A most preferred embodiment provides for a front and a back inspection unit having sensors disposed about their girths in a displaced fashion and which can be axially moveable relative to each other. The expansion of sensors located on arms of such a pig causes an increase in their angular separation within an inspection unit. On the other hand, one must inspect the pipe conduit about its entire periphery. This is fundamentally possible in that sensors, when appropriately axially displaced, are disposed in such a fashion as to cover the entire periphery of the pipe. Since however the signals from the individual sensors have to be correlated and in particular since, when passing though curves in the pipe conduit, the relative angular positions of the sensors, possibly provided on two differing inspection units, does not remain defined, it is therefore advantageous to completely cover the entire girth of the pipe conduit with sensors at one axial position. This is accomplished in the above mentioned preferred embodiment in that the inspection units are capable of displacement towards each other in such a fashion that the mutually angular-displaced sensors of the two inspection units occupy the same axial position. This guarantees that the entire girth of the pipe is covered by sensors and appropriately inspected at a common axial position when the device for inspection of pipe conduits is expanded.

In order to avoid difficult and expensive active displacement mechanisms for the inspection units which would require their own drive and power supply (the providing of sufficient electrical power to a pig is difficult since this must be supplied in the form of batteries or rechargeable batteries over substantial lengths and over long periods of time), the invention provides, in a most preferred improvement, that the rear inspection unit be moveable towards the front inspection unit under the action of the flow pressure of the fluid flowing in the pipeline, wherein, in particular, the back inspection unit can be moved towards the front inspection unit by means of a pull unit. The pull unit thereby has a collar which seats under the action of fluid pressure on the inner wall of the pipe conduit and is also pushed in a forward direction under the pressure of the flowing fluid such that it moves together with the rear inspection unit in the direction of motion of the inspection pig and in the direction of motion of the device for inspection of the pipeline conduits in a manner more rapid than the front inspection unit (relative to an external stationary point) to thereby more towards the front inspection unit. Since the extensive additional elements of an inspection pig such as electronic units, power supply units etc. are connected to the rear inspection unit and the pull unit, the front inspection unit moves relative to this residual portion of the inspection pig.

Further preferred embodiments of the invention provide that the inspection units are fixed relative to each other in certain angular positions, wherein, in particular, the sensors of the inspection units are disposed in angular displaced positions in such a manner that a sensor of the front inspection unit has an angular position midway between two neighboring sensors of the rear inspection unit with sensors of an inspection unit being aligned with each other.

A preferred embodiment provides that the inspection units can radially expand under the action of a spring force. In this manner, one guarantees that the sensors of the inspection units are pushed closely against the inner wall of the pipe conduit, wherein a predetermined defined separation can be effected by guide rollers mounted to a sensor support along with the sensors to guarantee that the sensors are located at a small defined radial separation from the inner wall of the pipe conduit while not coming in contact therewith, to prevent wear. A further improved embodiment can provide that the sensors be disposed on parallelogram rods. In this manner a stable configuration of the expandable inspection unit system is created, wherein one guarantees that, independent of the expansion position, the sensors always remain constantly parallel to the axis.

An additional preferred configuration is characterized by a releasable blocking mechanism to axially fix one of the inspection units, in particular the front inspection unit, to a guide element (guide rod), wherein, in particular, a release mechanism for releasing the blocking mechanism is provided when the corresponding inspection unit has reached its expansion position. This guarantees that, in the introductory position of the inspection unit, the front inspection unit is blocked on a guide rod at an axial separation with respect to the rear inspection unit and can not move relative thereto to prevent damage. One simultaneously guarantees that, when a predetermined radially expansion position is reached, the blocking mechanism is released so that the above mentioned relative motion between the two inspection units can transpire and the inspection units can move towards each other in an axial direction so that their sensors can occupy the desired common axial position (with angular displacements).

Further advantages and features of the invention can be extracted from the claims and the following description in which embodiments of the device in accordance with the invention are described more closely with reference to the drawing.

BRIEF DESCRIPTION OF THE DRAWING

FIG. 12 shows the progression of the expansion of the device in accordance with the invention during transition from a narrow introductory pipe into a wider pipeline being inspected.

DESCRIPTION OF THE PREFERRED EMBODIMENT

Figure 1:
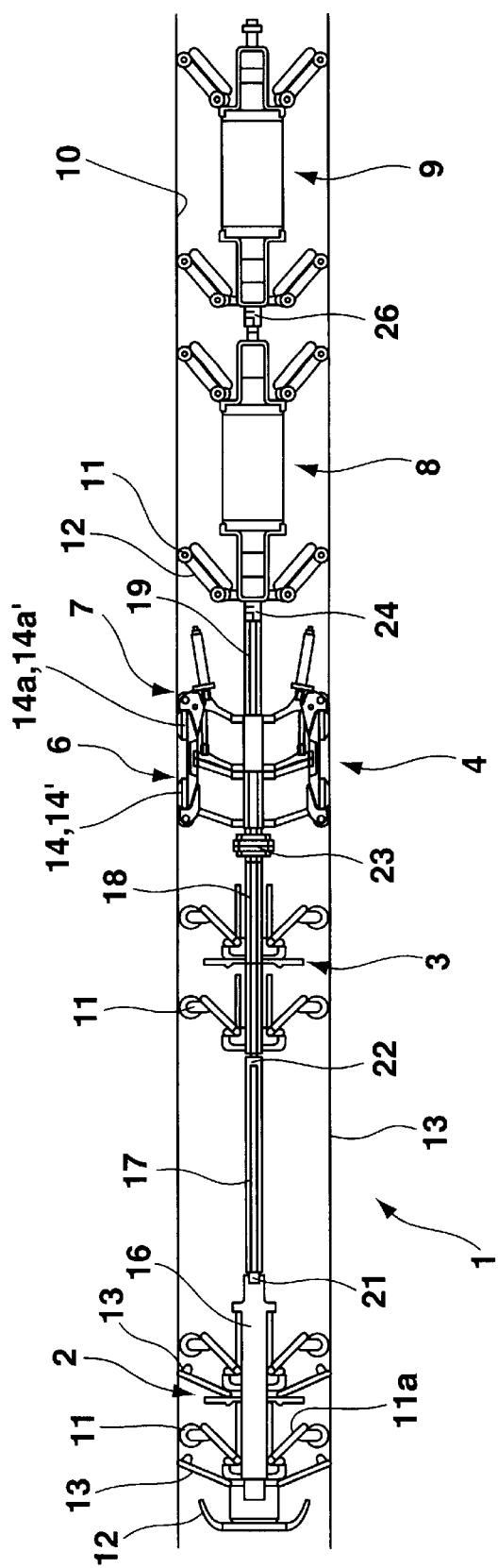
FIG. 1 shows a complete inspection pig located within a pipe conduit having a large diameter during inspection operation having expandable inspection units in accordance with the invention which can move into each other.

FIG. 1 shows an inspection pig for the inspection of pipe conduits 10 having an inspection device in accordance with the invention. In the embodiment shown, the pig 1 comprises a pull unit 2, a guide unit 3, the inspection unit 4 in accordance with the invention having, in the representation of FIG. 1, a front inspection unit 6 and a rear inspection unit 7 which can move into each other. An inspection pig 1 of this type normally has an additional electronic unit 8 and a power supply 9 having batteries or storage batteries. The individual units are guided in the pipe conduit 10 by means of wheels 11 disposed on arms 11a pushed in an outward direction by springs. Such an inspection pig moves within a pipeline in response to the flow pressure of the medium transported in the pipeline, and in the embodiment shown, by means of collars 12, 13. The collar 12 is designed for a pipe conduit having a narrow diameter, in the example shown, in the range between 26 and 28 inches, whereas the collars 13 are inactive in such a narrow pipeline. However, when the inspection pig 1 in accordance with the invention passes into a wider conduit, e.g. one having a diameter on the order of 40–42 inches, these can expanded to take over the drive function for the inspection pig 1. Inspection units 6 have sensors 15, 15' about their outer periphery which, in the embodiment shown, can be magnetic sensors, e.g. for inspection of the pipeline by means of stray magnetic field techniques, or other types of sensors.

The modules 2, 3, 4 seat on guide rods 16 through 19 which are connected to each other by means of linkages 21 through 23. The electronic unit 8 is connected to the inspection unit 4 via an additional linkage 24 and the power supply unit 9 is connected to the electronic unit 8 via a linkage 26.

In this manner, the inspection pig 1 can also be guided through pipe conduits having narrow radii of curvature. An inspection pig must not be precisely equipped with the inspection device in accordance with the invention as disclosed in this embodiment. For example, the electronic and power supply modules can be integrated within each other or be combined with other units.

Figure 2:
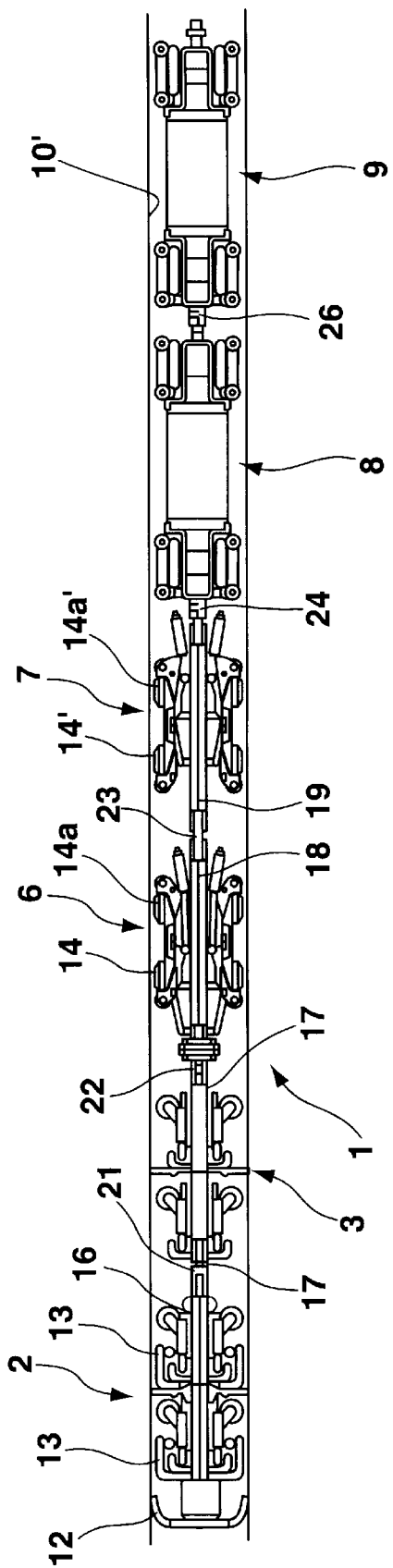
FIG. 2 shows the inspection pig of FIG. 1 in a compact introductory state within an introductory pipe having a narrower diameter.

Whereas FIG. 1 shows the inspection pig having an inspection device in accordance with the invention in an expanded operating state of the inspection device 4 in which the two inspection units 6, 7 are expanded and axially displaced within each other, FIG. 2 shows the same inspection pig 1 in an introductory state with which the two inspection units 6, 7 are axially apart, disposed at a separation with respect to each other, and radially compressed, as is also the collar 13 of the pull unit 2.

Figure 3:
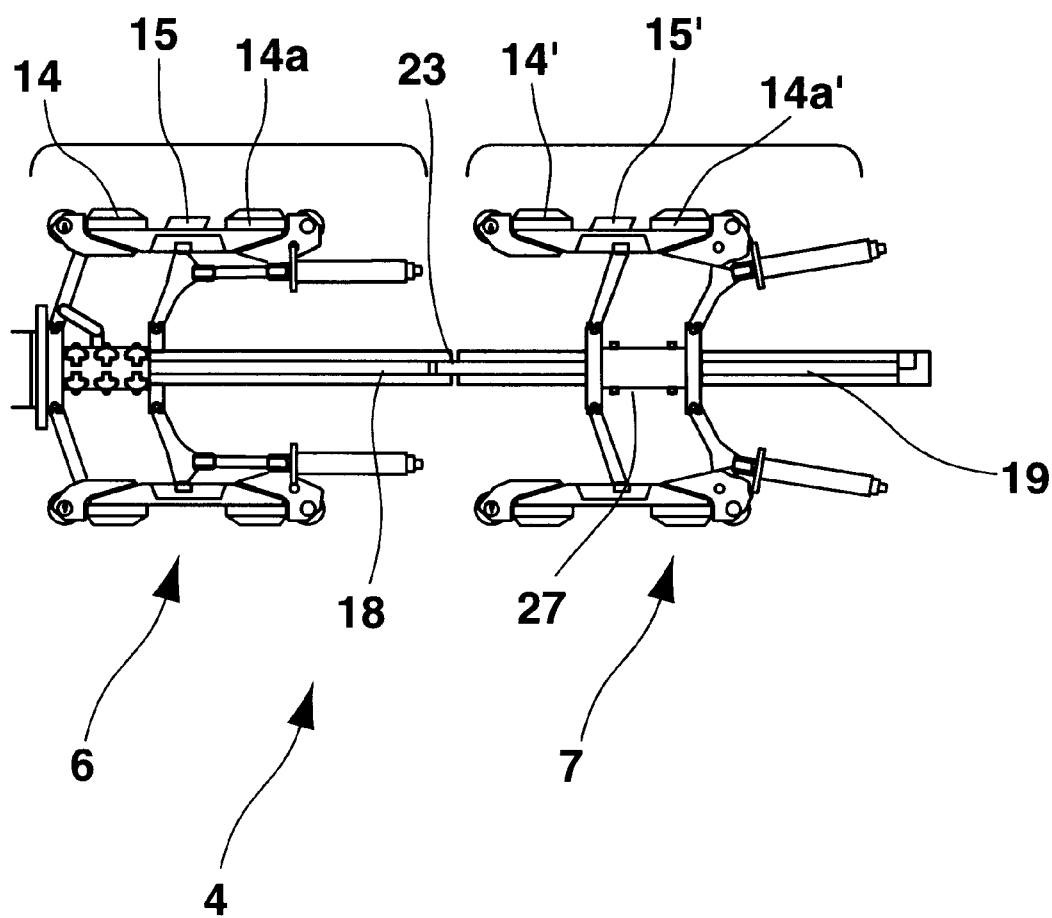
FIG. 3 shows the inspection device in accordance with the invention in the expanded state before the two inspection units have moved axially into each other.
Figure 4:
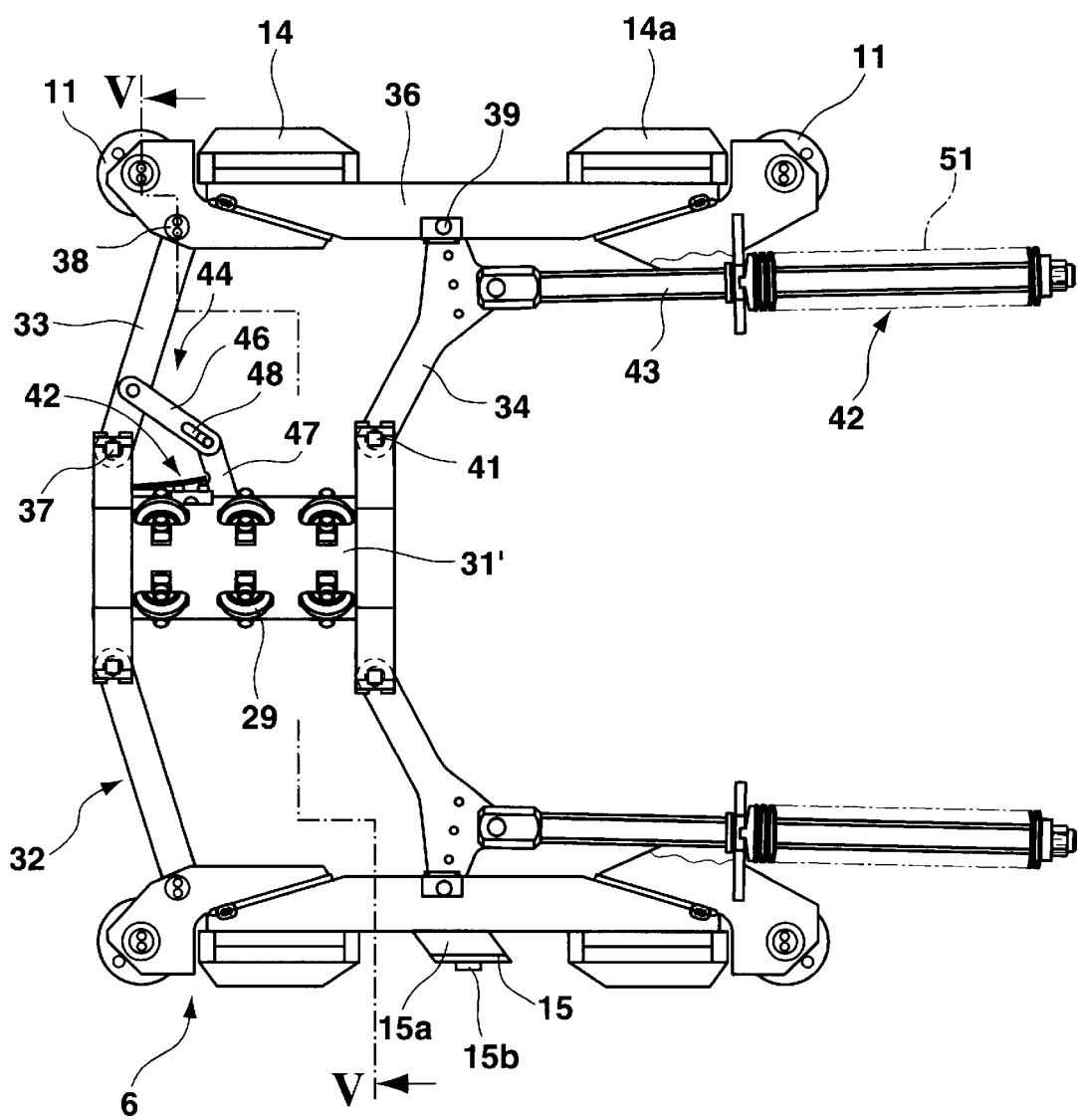
FIG. 4 shows a side view of the front inspection unit.
Figure 5:
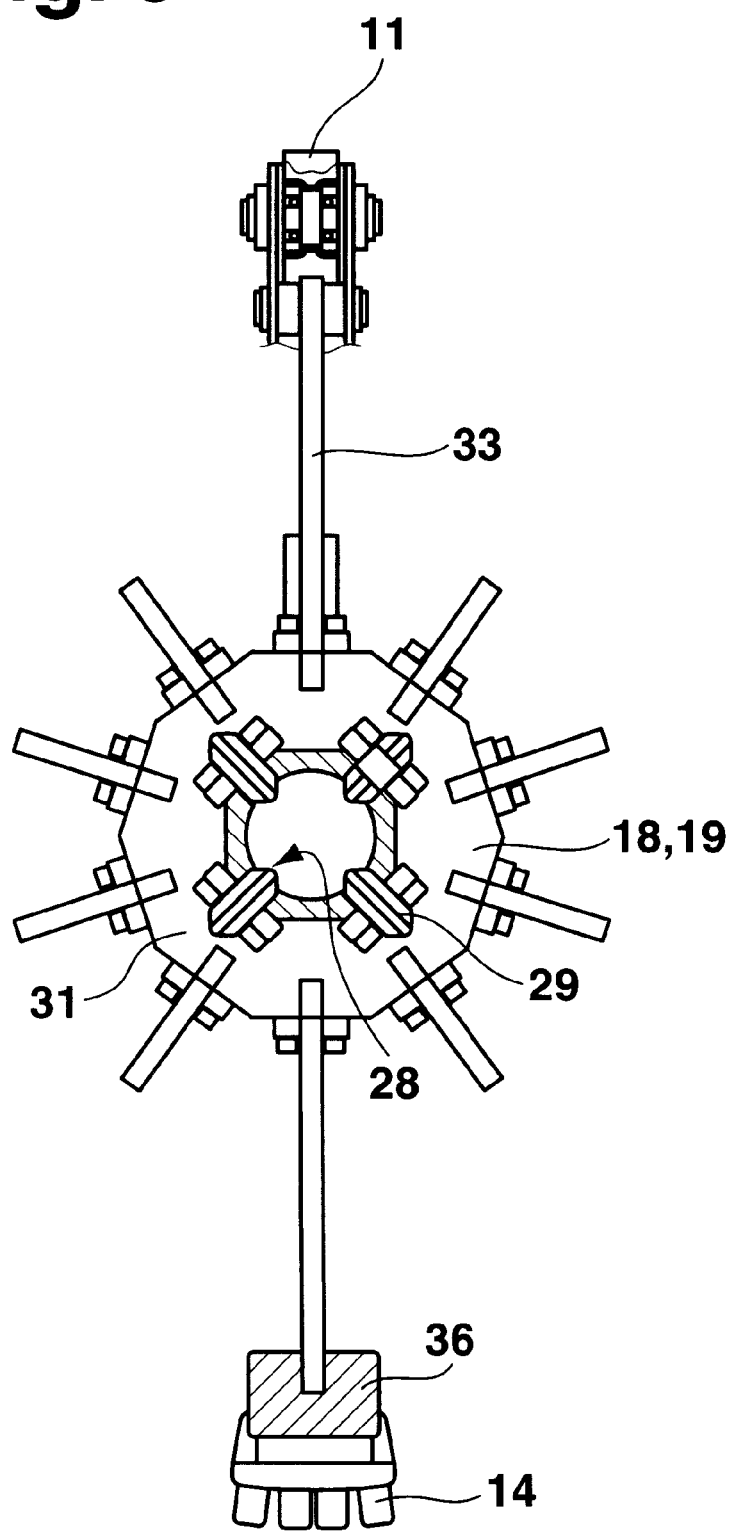
FIG. 5 shows a cut through the front inspection unit corresponding to V—V of FIG. 4.
Figure 7:
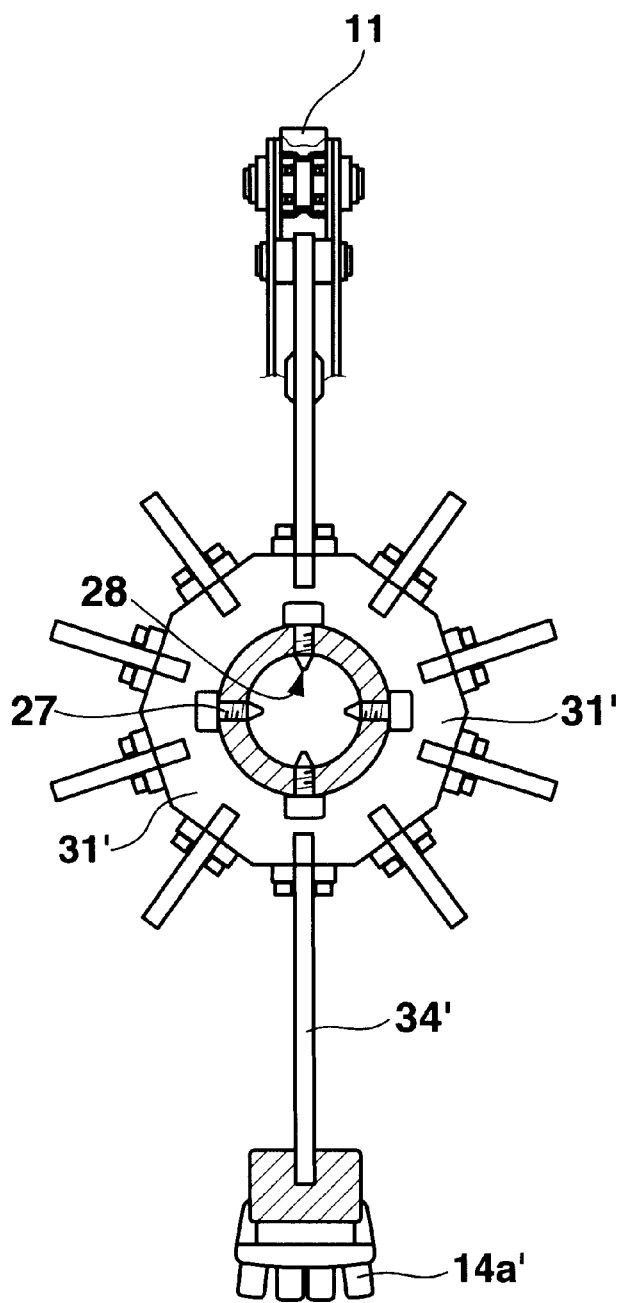
FIG. 7 shows a cut through the rear inspection unit corresponding to VII—VII of FIG. 6.

FIG. 3 shows the inspection device 4 in accordance with the invention in an expanded state with which the two inspection units 6, 7 are expanded such that their radii are adjusted to the pipe conduit of larger diameter which is to be inspected. The two inspection units 6, 7 are however not yet axially displaced within each other, rather still have an axial separation corresponding to the compressed introductory state through a narrow pipe conduit as shown in FIG. 2. They are thereby disposed on both sides of the linkage 23 on rods 18, 19, wherein the inspection unit 7 is axially fixed to the rod 19 via bolts 27 and the inspection unit 6 is guided in an axially displaceable fashion along the rod 18 past the linkage 23 and up to the rod 19. It is, however, guided or fixed in the angular direction relative to the rod 18, 19 and thereby aligned with respect to inspection unit 7. Towards this end, the rods 18, 19 (see, in particular, FIGS. 4 and 5) have axis-parallel guiding grooves 28 into which guide rollers 29 of the main body 31 of the inspection unit 6 engage to fix same at certain angular positions along the rods 18, 19. Bolts 27 likewise engage, as can be seen in FIG. 7, into guide grooves 28 of the rod 19 so that the inspection unit 7 is fixed both axially and in an angular manner. A comparison between FIGS. 5 and 7 shows that the sensors 15 of the front inspection unit 6 and sensors 15' of the rear inspection unit 7 are radially displaced with respect to each other in such a manner that the sensors 15 of the inspection unit 6 can engage into the intermediate angular spaces between two peripherally adjacent sensors 15' of the inspection unit 7 when e.g. the bolts 27 and the rollers 29 (FIGS. 5 and 7) engage in precisely the same guide groove (designated in the figures with the reference symbol 28).

Each inspection unit 6, 7 has a central main body 31, 31' with which it can be guided and fixed in the above mentioned fashion along and to rods 18, 19.

The sensors 15 and 15' respectively are supported on the main bodies 31, 31' via parallelogram rods 32, 32'. The parallelograms 32, 32' consist essentially of the main body 31, 31' front and rear connecting arms 33, 34 and 33',34' respectively and the forward sensor support 36 and backward sensor support 36' which are thereby guided parallel to the main body 31, 31'.

Figure 6:
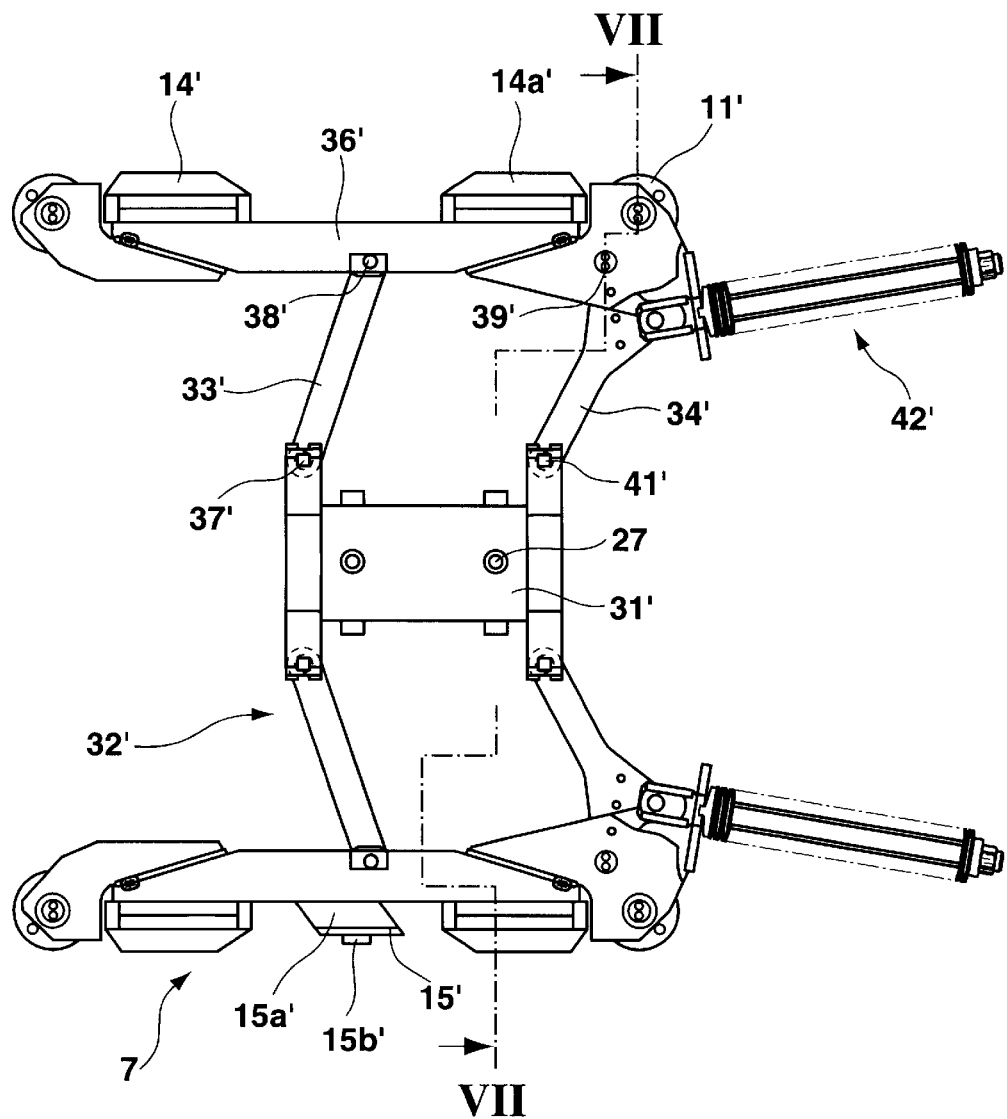
FIG. 6 shows a side view of the rear inspection unit.

Each sensor support 36, 36' supports pole shoes 14, 14a, 14', 14a' respectively at its outer side which are aligned one behind the other and parallel to the axis. These can e.g. be in the form of brushes which rub against the inner wall of the pipe conduit to thereby introduce a magnetic field into the pipe which can be detected by the sensors 15 and 15' respectively. The sensors themselves are borne in an elastic and resilient fashion on elastic supports 15a, 15a' (for example made from polyurethane) having a longitudinal section which is parallelogram in shape. A ceramic member 15b and 15b' respectively (FIGS. 4 and 6) is provided on the outer side to protect against wear.

The members 31, 33, 34, 36 of the parallelogram rods 32 and the members 31', 33', 34', 36' of the parallelogram rods 32' are linked to each other by means of linkages 37 through 39, 41 and 37' through 39', 41' such that the sensor supports 36, 36' are guided parallel to the corresponding main body 31, 31' independent of their radial position.

The sensor supports 36, 36' having the sensors 15 and 15' respectively are pressed via spring units 42, 42' into their radial extended position. The spring units 42, 42' comprise a disk spring 51 or helical springs.

Figure 8:
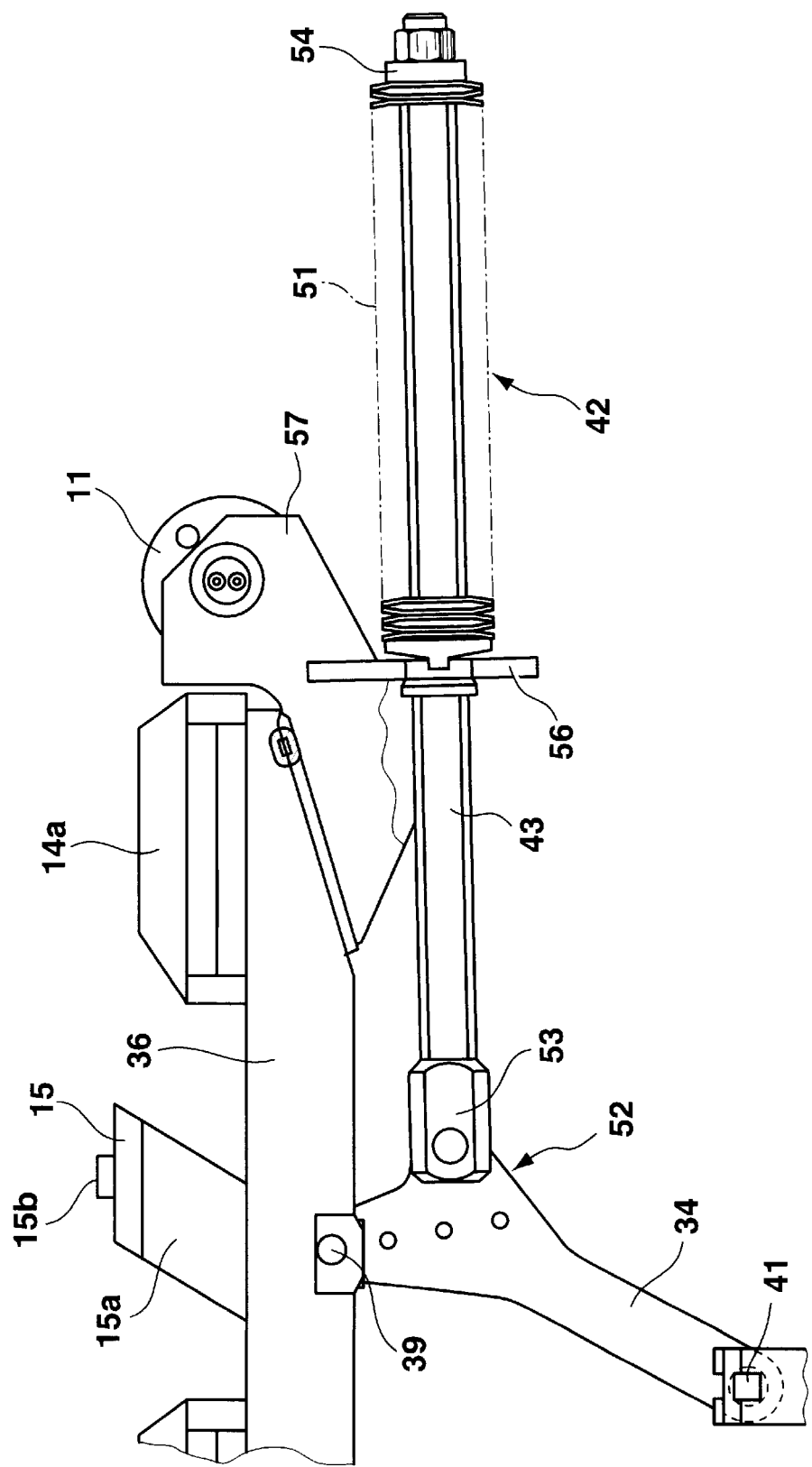
FIG. 8 shows a spring unit for radial erection of the inspection unit.

The spring unit 42 is shown in an enlarged manner in FIG. 8. An end 53 of a piston rod 43, 43' is linked to the respective spring unit 42, 42' at a location 52 between the linkages 39 and 41 or 39' and 41' respectively of the connecting arms 34 and 34' respectively. The spring 51 is tensioned between two abutments 54, 56. The abutment 54 is disposed on an end of the piston rod 43 opposite end 53 thereof. The abutment 56 is formed by a plate through which the piston rod 43 penetrates and which is fixed to a roller support 57 for the roller 11 connected to the sensor support 36. The spring unit 42' is correspondingly configured. The spring action of the spring unit 42, 42' attempts to shorten the free region of the piston rod 43 between the end 53 and the abutment 56 and thereby to radially erect or to expand the parallelogram rods 32 (or 32') so that the inspection unit can radially expand during transition from a pipe of low diameter into a pipe of larger diameter.

Figure 9:
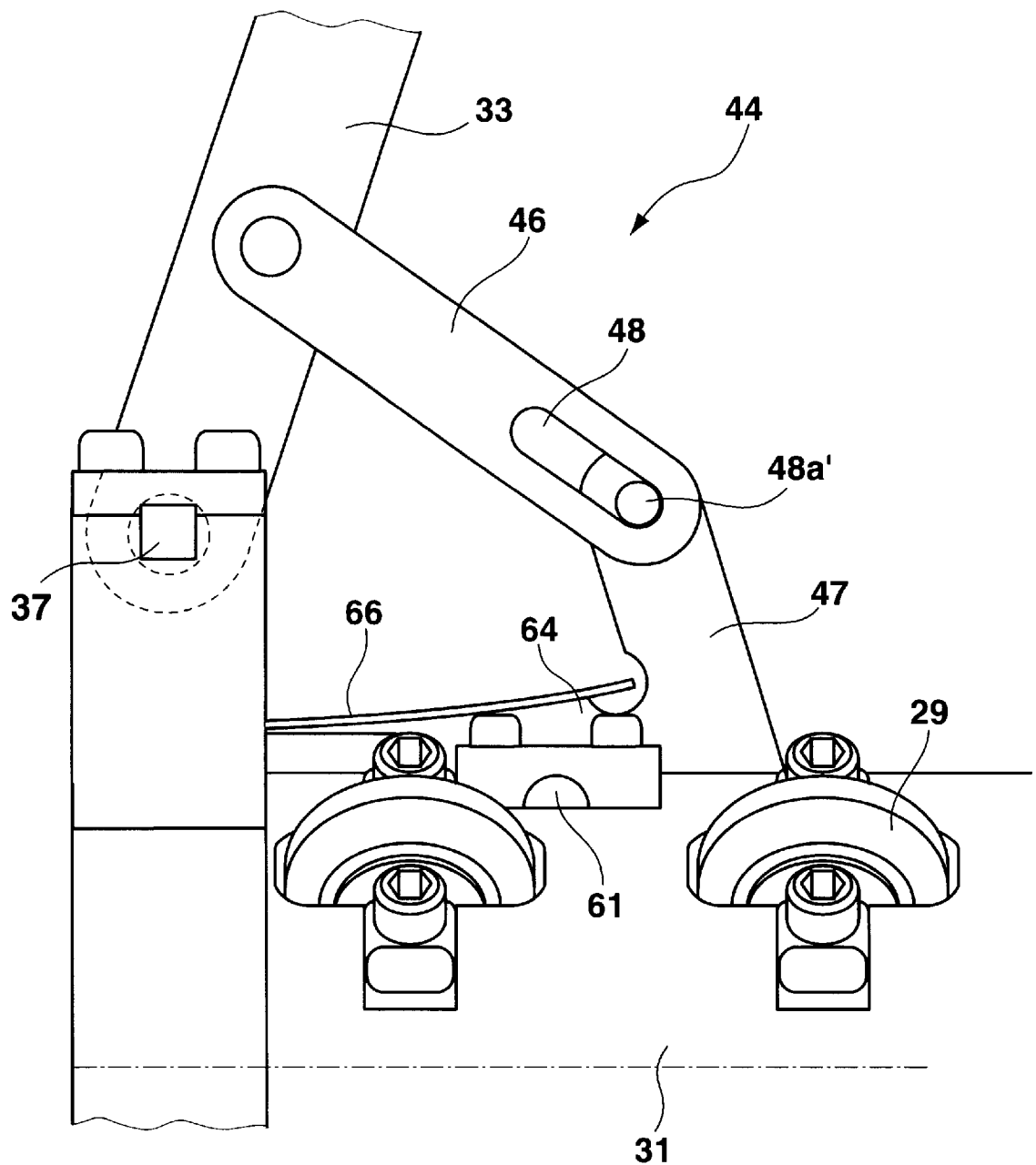
FIG. 9 shows a blocking and releasing mechanism to release one of the inspection units for axial displacement.
Figure 10:
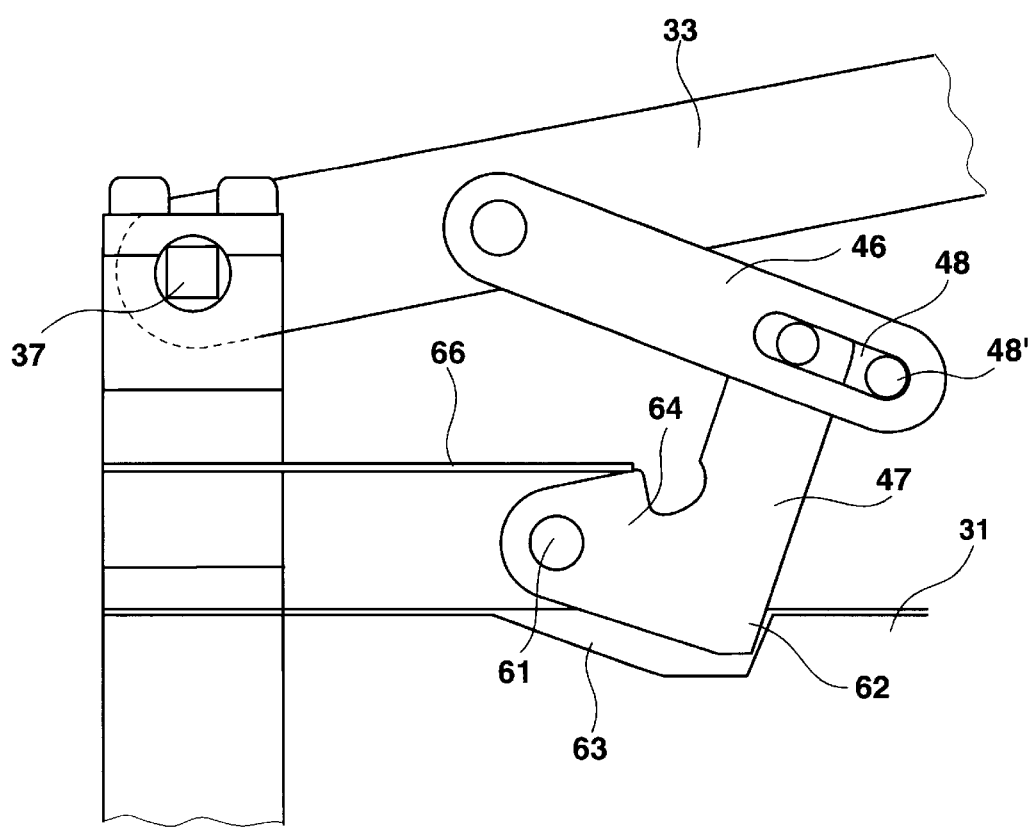
FIG. 10 shows a part of the blocking and releasing mechanism in the blocking position.
Figure 11:
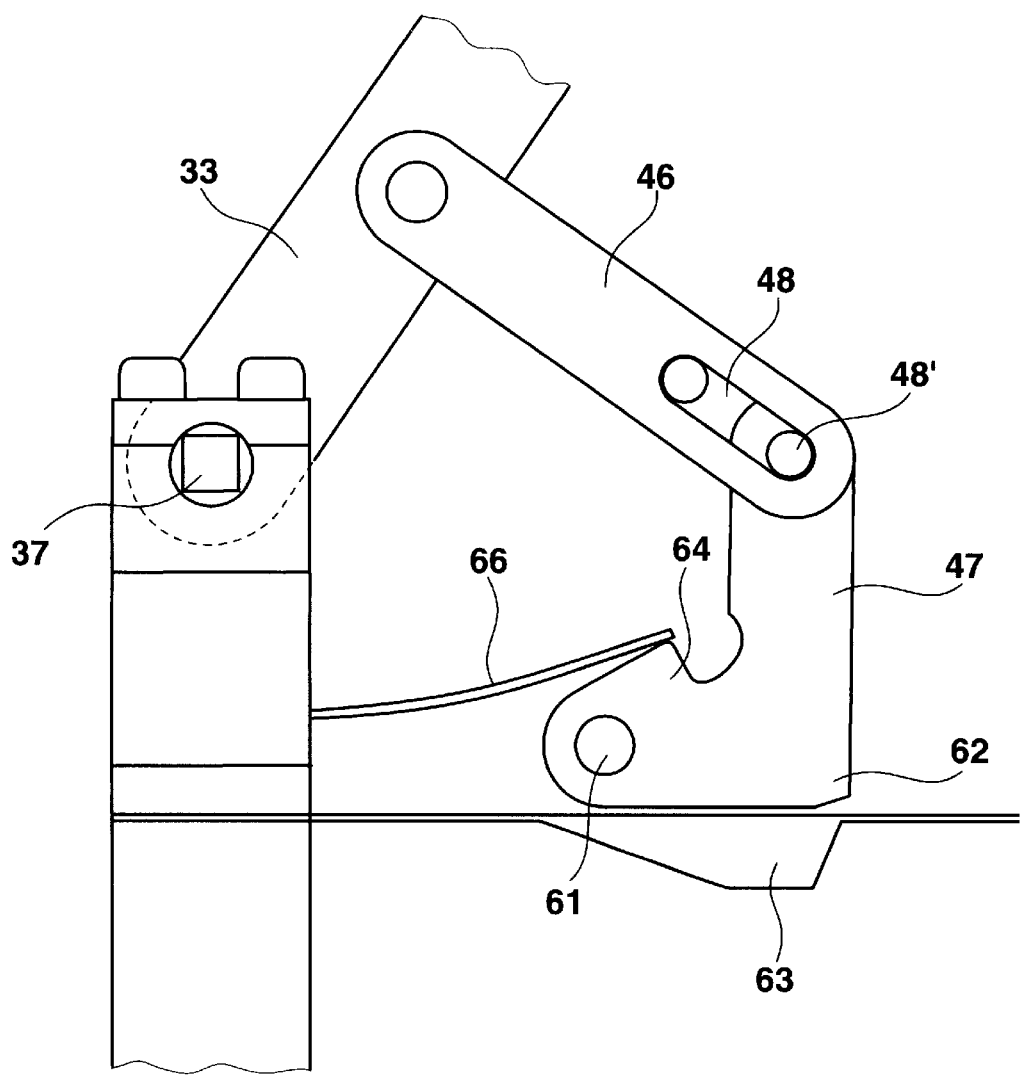
FIG. 11 shows the part of the blocking and releasing mechanism of FIG. 10 in the releasing position.

The inspection unit 6 has a blocking and releasing mechanism 44 for axially blocking and releasing the motion along the rods 18, 19 (FIG. 9). The blocking and releasing mechanism has an arm 47 hinged to a connecting arm 33 and an arm 47 connected to the main body 31 which are linked for relative motion towards another by a slot in arm 46 and a pin 48a in arm 47 engaging therein. The arm 47 is linked in a pivotable fashion at 61. In the compressed state of the inspection unit, the arm 47, at an end facing away from the arm 46, passes through the body 31 and engages into an opening 63 in the rod 18 to thereby block the inspection unit 6 with respect to displacement along the rods 18, 19 (FIG. 10). A leaf spring 66 bears on a outwardly directed shoulder 64 and thereby presses the arm 47 into its radially inward position. If the inspection unit 6, when passing from a pipe of small diameter into a pipe of larger diameter, then expands under the action of spring unit 42 so that the parallelogram rods 32 radially erect, the arm 46 is carried by the arm 33 but, due to the slot 48, can nevertheless move relative to the arm 47 which, in turn, is initially held stationary by means of the leaf spring 66 and blocks, by means of its shoulder 62 engaging into the opening 63 of the rod 18, the inspection unit 6 on the rod 18 even during its radial expansion. When a predetermined radial diameter is reached, the arm 46 carries the arm 47, in opposition to the action of the leaf spring 66, along with it and pivots same so that its shoulder 62 leaves engagement with the opening 63 of the rod 18 (FIGS. 9, 11) to thereby release axial motion of the inspection unit 6 such that it can, via the pig motion, move along the rod 18, 19 towards the inspection unit 7.

As soon as the parallelogram rods 32 have radially erected, a blockage is thereby released which, in the compressed introductory state of the inspection unit 6 blocks same axially on the guide rods 18. After release, the inspection unit 6 can travel via its rollers 29 along the guide rods 18 and past the linkage 23 along the guide rods 19 towards the inspection unit 7.

The expansion of the inspection unit 4 in accordance with the invention and the axial moving together of the inspection units 6 and 7 transpires in the following manner (FIG. 12).

The inspection pig, having the inspection device in accordance with the invention, is initially guided through a pipe conduit 10' having a reduced diameter of e.g. approximately 28 inches while disposed in its radially compressed position shown in FIG. 2. It is pushed through the pipe conduit 10' by means of its collar 12 since same enters tightly into the pipe conduit 10' so that the upstream pressing fluid can press the inspection pig 1, substantially via the collar 12, through the pipe conduit 10'.

As soon as the collar 12 and the front collar 13 have gained entrance into the transitional region 10" between the narrower pipe conduit 10' and the additional pipe 10, the most forward erecting collar 13 can initially expand since it presses firmly against the wall of the transitional region 10" and of the pipe 10 to thereby drive the inspection pig 1 (phase 2). In phase 3, the rear erecting collar 13 also expands. The pig is pulled further out of the narrow pipe 10' past the transitional region 10" into the additional pipe 10 (phases 4, 5). As soon as the front inspection unit 6 passes through the transitional region 10" it expands thereby under the action of its spring units 42. As soon as the inspection unit 6 has assumed its fully expanded position, the blocking and releasing mechanism 44 releases the inspection unit 6 in a manner described with respect to FIG. 9 so that the inspection unit 6 can move along the rods 18, 19 and past linkage 23 (phases 6, 7). The relative motion of the inspection units 6, 7 towards each other is due to the fact that, subsequent to release, the inspection unit 6 is held on the inner wall of the pipe conduit 10 by friction, whereas the inspection unit 7 which is fixed to the rod 19 is pulled further in the direction of motion of the inspection pig (arrow A) by means of the collar 13 and via the rods 16,17, 18 to thereby move towards the inspection unit 6. The entire inspection pig, with the exception of inspection unit 6, and in particular along with inspection unit 7, thereby carries out a larger relative motion relative to a stationary observer in the direction of arrow A than the inspection unit 6 (which moves relative to the overall remaining inspection pig and in particular with respect to and towards the inspection unit 7). In the embodiment shown, the guide unit 3 is connected to the inspection unit 6 to thereby carry out together therewith the relative motion with respect to the remaining pig 1, as can be likewise extracted from the phases 6 through 8. When the inspection unit 7 completely enters into the additional pipe conduit 10, the inspection units 6, 7 have moved axially within another in such a fashion that the front sensors 15 and the rear sensors 15' of the two inspection unit 6, 7 both occupy a common axial position while being, however, displaced with respect to angle in the manner described above. In this manner, a sensor 15 engages into each free angular space between two sensors 15' and vice versa.

The pig is then located (phase 8) in its inspection position and can carry out an inspection of the walls of the pipe of the additional conduit 10 to locate defects.

We claim:

1. A device for the inspection of a pipe conduit, the pipe conduit having a first region with a first diameter and a second region with a second diameter larger than the first diameter, the device comprising:
   a first inspection unit comprising a first array of sensors mounted at an outer periphery thereof at first spaced angular positions;
   a second inspection unit comprising a second array of sensors mounted at an outer periphery thereof at second spaced angular positions having an angular offset with respect to said first spaced angular positions, said second inspection unit disposed for axial displacement thereof towards and away from said first inspection unit in response to a diameter of the pipe conduit, wherein said second inspection unit is axially displaced from said first inspection unit in the first region of the pipe conduit and said first array of sensors is disposed between said second array of sensors in the second region of the pipe conduit;
   a guide element to guide said inspection units; and
   a releasable blocking mechanism for axially fixing one of said inspection units to said guide element.

2. The device of claim 1, wherein said sensors of said inspection units are disposed at angles offset with respect to each other in such a manner that a sensor of a front inspection unit is disposed at an angular middle between two neighboring sensors of a rear inspection unit.

3. The device of claim 1, wherein said guide element guides a front inspection unit and said releasable blocking mechanism axially fixes said front inspection unit to said guide element.

4. The device of claim 3, further comprising a releasing mechanism for releasing said blocking mechanism in an expanded position of said front inspection unit.

5. The device of claim 1, wherein a rear inspection unit moves toward a front inspection unit under a flow pressure of fluid flowing in the pipe conduit.

6. The device of claim 1, wherein a pull unit moves a rear inspection unit towards a front inspection unit.

7. The device of claim 1, further comprising means for holding said inspection units in particular angular positions relative to each other.

8. The device of claim 1, wherein sensors of an inspection unit are disposed axially aligned with respect to each other.

9. The device of claim 1, wherein said inspection units radially expand under an action of a spring force.

10. The device of claim 1, wherein said inspection units comprise parallelogram rods for supporting said sensors.

11. The device of claim 1, further comprising a releasing mechanism for releasing said blocking mechanism when an expansion position of said one of said inspection units has been reached.

12. The device of claim 1, wherein said second inspection unit is a front inspection unit and said first inspection unit is a rear inspection unit.

* * * * *